United States Patent
Fresu

(10) Patent No.: US 12,042,520 B2
(45) Date of Patent: Jul. 23, 2024

(54) COMPOSITIONS CONTAINING CURCUMIN HAVING IMPROVED BIOAVAILABILITY

(71) Applicant: SOLUVEG SA, Luxembourg (LU)

(72) Inventor: Antonello Fresu, Roodt sur Syre (LU)

(73) Assignee: Gianluca Fresu, Le Bosc Roger en Roumois (FR)

( * ) Notice: Subject to any disclaimer, the term of this patent is extended or adjusted under 35 U.S.C. 154(b) by 329 days.

(21) Appl. No.: 15/542,371

(22) PCT Filed: Jun. 30, 2015

(86) PCT No.: PCT/EP2015/064855
§ 371 (c)(1),
(2) Date: Jul. 7, 2017

(87) PCT Pub. No.: WO2016/110334
PCT Pub. Date: Jul. 14, 2016

(65) Prior Publication Data
US 2017/0368115 A1 Dec. 28, 2017

(30) Foreign Application Priority Data

Jan. 7, 2015 (LU) .......................... 92 630

(51) Int. Cl.
*A61K 35/748* (2015.01)
*A61K 9/00* (2006.01)
*A61K 31/12* (2006.01)
*A61K 36/9066* (2006.01)

(52) U.S. Cl.
CPC .......... *A61K 35/748* (2013.01); *A61K 9/0053* (2013.01); *A61K 31/12* (2013.01); *A61K 36/9066* (2013.01)

(58) Field of Classification Search
None
See application file for complete search history.

(56) References Cited

U.S. PATENT DOCUMENTS

| | | | |
|---|---|---|---|
| 2007/0122496 A1 | 5/2007 | Managoli | |
| 2008/0260695 A1* | 10/2008 | Lu | A61K 36/07 424/93.4 |
| 2012/0251500 A1 | 10/2012 | Cappello | |

FOREIGN PATENT DOCUMENTS

| | | |
|---|---|---|
| DE | 19906016 A1 | 8/2000 |
| FR | 2949646 A1 | 3/2011 |

OTHER PUBLICATIONS

Guido Shoba et al. "Influence of piperine on the pharmacokinetics of curcumin in animals and human volunteers" Planta Medica, May 1998; vol. 64, No. 4, pp. 353-356.
International Search Report issued Aug. 27, 2015 re: Application No. PCT/EP2015/064855; pp. 1-3; citing; US 2008/260695 A1, US 2007/122496 A1, DE 199 06 016 A1, FR 2 949 646 A1 and US 2012/251500 A1.
Written Opinion issued Aug. 27, 2015 re: Application No. PCT/EP2015/064855; pp. 1-6; citing; US 2008/260695 A1, US 2007/122496 A1, DE 199 06 016 A1, FR 2 949 646 A1 and US 2012/251500 A1.
Zhang et al., "Pharmacokinetics and absolute bioavailability of curcumin in rats", Chinese Pharmacological Bulletin, Oct. 2011, 27(10), pp. 1458-1462 (with English translation).
U.S. Environmental Protection Agency, "Provisional Peer-Reviewed Toxicity Values for 1,1-Dimethylhydrazine (CASRN 57-14-7)", Final, EPA/690/R-09/018F, Sep. 30, 2009, 34 pages.

* cited by examiner

*Primary Examiner* — Vera Afremova
(74) *Attorney, Agent, or Firm* — CANTOR COLBURN LLP

(57) ABSTRACT

The invention relates to the pharmaceutical or non-pharmaceutical use of an effective amount of *spirulina* and/or of an extract/extracts of *spirulina* for improving the bioavailability of orally administered curcumin in humans or animals. The invention also includes pharmaceutical or non-pharmaceutical preparations including *spirulina* and/or extracts of *spirulina* containing curcumin having improved bioavailability.

15 Claims, 2 Drawing Sheets

Kinetics of orally administered Curcumin S1 in the horse

Time/hours

Kinetics of Curcumin SOLUVEG

Time/hours

Kinetics of intravenously administered Curcumin in the pig

COMPOSITIONS CONTAINING CURCUMIN HAVING IMPROVED BIOAVAILABILITY

TECHNICAL FIELD

The present invention relates generally to compositions comprising curcumin, whose bioavailability is considerably improved with respect to known compositions.

BACKGROUND

Curcumin is a natural phenol and has long been used not only in the nutritional field (mainly as a colorant), but also for its health benefits. In fact, curcumin is a highly active antioxidant, an efficient antiseptic and antibacterial, as well as a powerful anti-inflammatory. Other beneficial effects are cited in the literature, in particular for diverse human and animal diseases, especially cancer, cardiovascular diseases, diabetes, arthritis, neurological diseases and Crohn's disease inter alia.

Unfortunately, it has been found that when used alone, curcumin is very rapidly eliminated by the body. Different studies on humans and especially the rat have shown that orally administrated curcumin exhibits a limited bioavailability, both because of the low intestinal absorption and because of high renal and biliary excretion. Other studies have demonstrated that intravenous administration of curcumin in rats leads to a biliary excretion of curcumin of more than 50% in 5 hours.

In pharmacy (but also in nutrition), the term bioavailability is used to describe a pharmacokinetic property of a compound, namely the fraction of a dose which, in its unchanged form, enters the bloodstream. This is an essential concept in pharmacokinetics because the bioavailability must be taken into account when calculating doses for routes of administration other than intravenous routes.

Above certain concentrations in the blood, curcumin is also known to produce a laxative effect in many animal species, particularly also in humans.

Consequently, any proposed solution should improve the bioavailability but without increasing the levels of curcumin beyond troublesome concentrations.

Numerous attempts have in fact been made to address the problem of the reduced bioavailability of curcumin. By way of example, reference is made to the use of piperine (present in black pepper) that is purported to inhibit the elimination paths of curcumin, thereby multiplying its bioavailability by a factor of 20 (Shoba G, Joy D, Joseph T, Majeed M, Rajendran R, Srinivas P S. Influence of piperine on the pharmacokinetics of curcumin in animals and human volunteers. Planta Med. 1998 May; 64(4): 353-6.). However, even though the bioavailability was improved, the blood level values were not optimal and the piperine produced an irritating effect in the intestine.

Other approaches to overcome the low bioavailability include, for example, the use of liposomal curcumin; the preparation of curcumin nanoparticles; the use of curcumin-phospholipid complexes; and the use of structural analogues of curcumin.

BRIEF SUMMARY

A subject matter of the present invention is therefore to propose compositions comprising curcumin which enable an improved bioavailability of curcumin in comparison to curcumin taken alone, wherein these compositions may serve, if need be, as alternatives to or to complement existing solutions.

To solve the abovementioned problem, the present invention proposes, in a first aspect, the pharmaceutical and non-pharmaceutical use of an effective quantity of *spirulina* and/or of *spirulina* extract(s) for improving the bioavailability of administered or orally administered curcumin in animals, in particular domestic animals or pets, such as the horse, the pig, the dog and the cat; or in humans.

The invention also proposes the use of an effective quantity of *spirulina* and/or of *spirulina* extract(s) and of curcumin for manufacturing oral pharmaceutical and non-pharmaceutical preparations of curcumin with improved bioavailability.

In a further aspect, the invention also relates to oral pharmaceutical and non-pharmaceutical preparations (particularly food supplements) comprising curcumin and an effective quantity of *spirulina* or of *spirulina* extract(s).

In fact, surprisingly for a person skilled in the art, the inventors have found that by combining curcumin with *spirulina* the bioavailability of curcumin is significantly increased when it is taken orally. Moreover, it was shown that the invention not only increases this bioavailability but also controls the maximum concentration in the blood and maintains it at a sufficient level for a longer period, i.e. increases the fraction of curcumin that is absorbed at the level of the intestine, and at the same time prolongs the presence of the curcumin at useful concentrations.

Although *spirulina* and *spirulina* extracts, due to their high nutritional value, have long been known as a food or food supplement, their beneficial effect on the bioavailability of curcumin taken orally remained unknown up to now.

In fact, generally speaking, the term *spirulina* is used to indicate a certain number of different cyanobacteria of the genus *Arthrospira*, notably *Arthrospira platensis* (sometimes called *Spirulina platensis*), but also *Arthrospira maxima*, *Arthrospira pacifica*, etc. This term also designates preparations based on these cyanobacteria, here as a food, but most frequently as food supplements, for example when dried and compressed. In the context of the present invention, the term *spirulina* may designate cyanobacteria or preparations containing them according to the context, wherein quantitative indications that refer to *spirulina* relate to the effective dry weight of the cyanobacteria of the genus *Arthrospira*. The terms *spirulina* extract or *spirulina* extracts in the context of the invention designate one or more extracts obtained from *spirulina* as defined above, i.e. one or more extracts of cyanobacteria of the genus *Arthrospira*, wherein the extract was obtained by a known extraction process, preferably the extract is an ethanol extract. The quantitative indications concerning the *spirulina* extracts refer, unless otherwise explicitly stated, to the dry weight of the extract.

The term effective quantity in the present invention means a quantity of *spirulina* and/or *spirulina* extract(s), which afford a major and significant positive effect on the bioavailability of curcumin taken orally. Although the actual value of this effective quantity may vary, particularly as a function of the animal in question or of other possible ingredients of the preparation, it is easy for the person skilled in the art to verify the effective quantity needed to obtain the desired effect in a given situation. This effective quantity is preferably expressed as a weight ratio of *spirulina* or *spirulina* extract to the quantity of curcumin whose bioavailability is improved. This weight ratio *spirulina*:curcumin (respectively *spirulina* extract(s):curcumin) is preferably comprised between 20:1 and 1:3, more preferably between 10:2 and 1:2, in particular between 8:3 and 3:4.

The quantity of curcumin comprised in the preparations according to the invention is, of course, dependent on a number of factors, including the desired effect, respectively the required indication, the animal considered, its size/weight, the presence of other ingredients or active principles, etc.

In practice, the quantities of curcumin to be used frequently range between 0.1 and 20 mg/kg, preferably between 0.5 and 15 mg/kg, more preferably between 1 and 10 mg/kg body weight, most preferably between 3.5 and 7.5 mg/kg.

Clearly, depending on the utility of the preparation and the animal to be treated, the preparation will comprise other active ingredients or not and therefore the concentration of curcumin in the preparation may vary widely.

The present invention envisages ready for use oral preparations, but also concentrated preparations to be mixed with common foods, as liquid or solid preparations, as powders, in the form of tablets or capsules. It should be noted that the invention explicitly foresees that the *spirulina* or its extracts are not necessarily taken at the same time or in a mixture with the curcumin in order to have the desired effect. It is also possible or conceivable to sequentially administer the *spirulina* and the curcumin (in any order, but preferably beginning with the *spirulina*), while ensuring, however, that the two administrations are preferably made within 1 hour, in particular within half an hour.

The disease to be treated or the reasons to administer the curcumin are numerous and the following examples do not limit the scope of the invention in any way, but rather serve to illustrate it.

Another aspect of the present invention relates to pharmaceutical and non-pharmaceutical preparations that additionally comprise other pharmaceutically active or health-beneficial ingredients. These ingredients may be selected from anti-inflammatory agents, analgesics, anti-cancer agents, vitamins, essential fatty acids, etc. These ingredients are preferably of natural origin, in particular the extracts of white willow (*Salix alba*), of boswellia (*Boswellia serrata*), of yucca (*Yucca schidigera*) and of Harpagophytum.

The preparations of the present invention can also comprise other ingredients that serve particularly to improve the composition in regard to the formulation, the taste, the consistency, the presentation, especially the colour, etc. These ingredients may be selected from among those generally known in the field according to the type of preparation and the desired outcome.

It should be noted that the preparations according to the invention may also comprise other components that could improve the bioavailability of the curcumin, for example piperine. It is also conceivable that the curcumin (or part of it) could be in the form of liposomal curcumin; of nanoparticles of curcumin; of phospholipid-curcumin complexes; and/or of structural analogues of curcumin.

Another aspect of the present invention relates to pharmaceutical and non-pharmaceutical preparations that comprise only curcumin and *spirulina* as the active ingredients, possibly with excipients and supports (pharmaceutically or nutritionally acceptable substances). Such preparations preferably consist of a combination of curcumin with *spirulina* and/or one or more *spirulina* extract(s).

In other words, the invention also envisages compositions comprising solely curcumin and an effective quantity of *spirulina* (or its extracts).

Finally, a further aspect of the invention relates to a manufacturing process for a preparation such as is described in this document, wherein the process comprises a step of mixing an effective quantity of *spirulina* and/or one or more *spirulina* extracts with curcumin, possibly with other active ingredients, excipients or supports, which are acceptable in the field of pharmacy or nutrition.

BRIEF DESCRIPTION OF THE DRAWINGS

Other distinguishing features and characteristics of the invention will emerge from the detailed description of several advantageous illustrative embodiments presented below, by referring to the appended figures. They show.

EXAMPLES

Materials and Method

A first composition comprising curcumin and *spirulina* was prepared by combining in the following order, with constant stirring and homogenisation, purified water, potassium sorbate, citric acid, sucrose, curcumin 95% (curcuminoid content: 95.7%, determined by HPLC), *spirulina* extract and Xanthan gum. The *spirulina* extract was obtained by dissolving 1 g of standard raw material in 20 ml water under reflux for 60 minutes. The aqueous extract was filtered then made into a dry concentrate in a desiccator under vacuum. The dry residue was then dissolved in 5 ml methanol so as to obtain the *spirulina* extract. This preparation is designated hereinafter as curcumin S1.

A first experiment to determine the bioavailability (pharmacokinetic study) of curcumin in the horse was carried out by determining the quantity of curcumin in the blood (plasma concentration).

The 3 selected horses were between 7 and 10 years old, each estimated to weigh 500 kg. The curcumin S1 was administered orally (2.6 grams of curcumin S1 for 500 kg of live weight, i.e. 5.6 mg/kg) in a single dose.

Plasma samples were taken prior to the administration (time T0) of the curcumin S1 preparation and 3 hours, 6 hours, 9 hours, 12 hours, 24 hours, 36 hours and 50 hours after administration of the preparation.

The samples were frozen at −18° C. until the analytical determination.

The technique used for the determination of the curcumin concentration in the plasma was HPLC (high performance liquid chromatography).

Results

The results of the mean curcumin concentrations in the plasma as a function of time are presented in Table 1.

TABLE 1

Curcumin concentration in the plasma after oral administration of a preparation curcumin S1 in the horse

| Time (hours) | Nanograms/millilitre |
|---|---|
| 0 | 0 |
| 3 | 230 |
| 6 | 260 |
| 9 | 280 |
| 12 | 410 |
| 24 | 350 |
| 36 | 150 |
| 50 | 0 |

Discussion

As can be seen, the curcumin concentrations in the plasma obtained with the preparation curcumin S1 are relatively high in relation to the orally administered single dose (2.6 grams of curcumin S1 for 500 kg of live weight, i.e. 5.6 mg/kg) with a plasma concentration peak at 12 hours and remaining almost constant for 12 hours (T12=410 ng/ml and T24=350 ng/ml).

Figure 1:
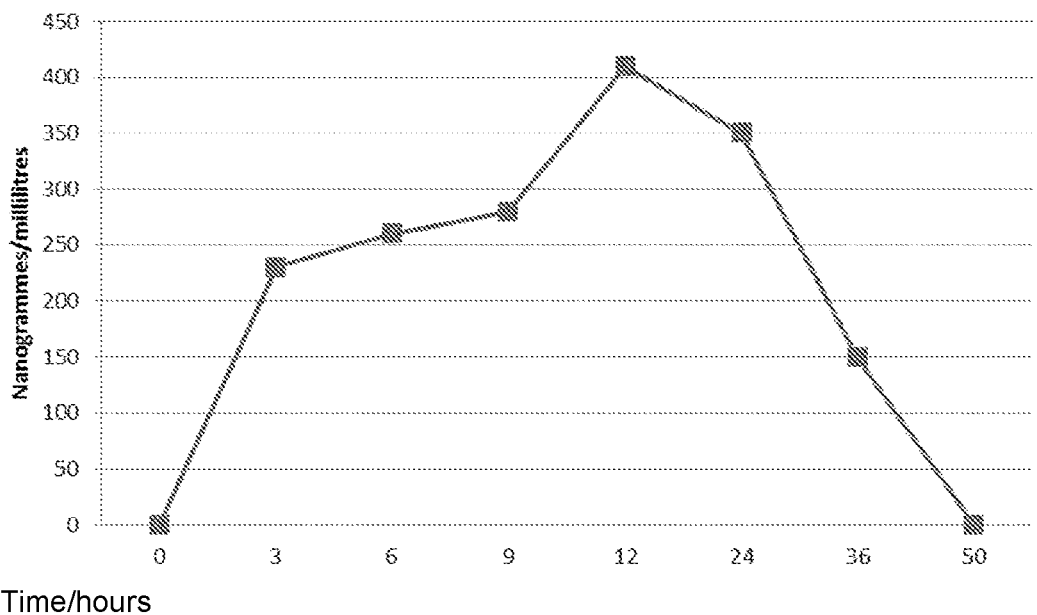
FIG. 1: is a graph representing the bioavailability (or the kinetics) of the curcumin preparation S1 according to the invention, administered orally to a horse.
Figure 1:
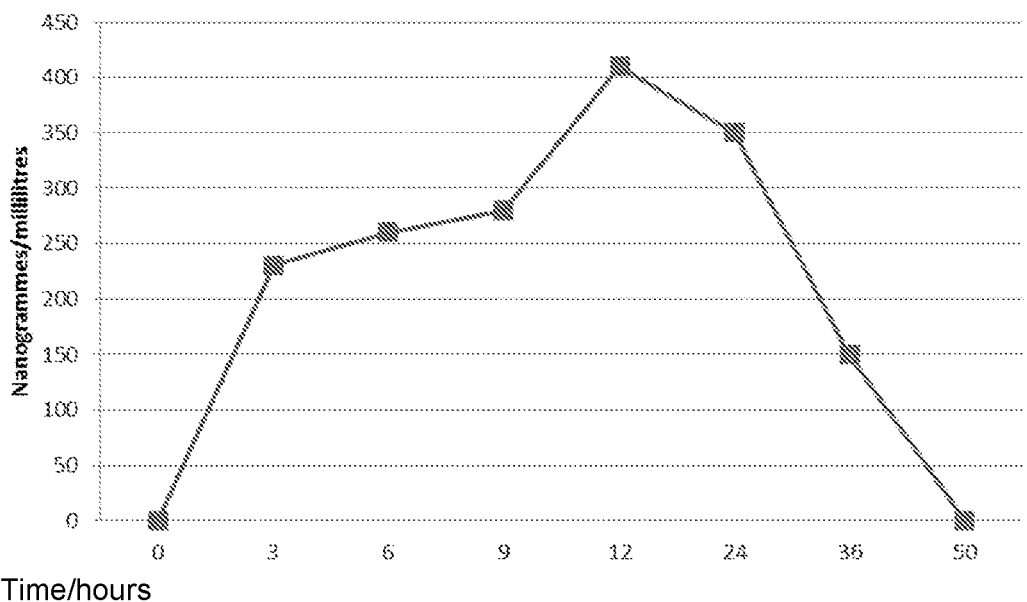
Figure 2:
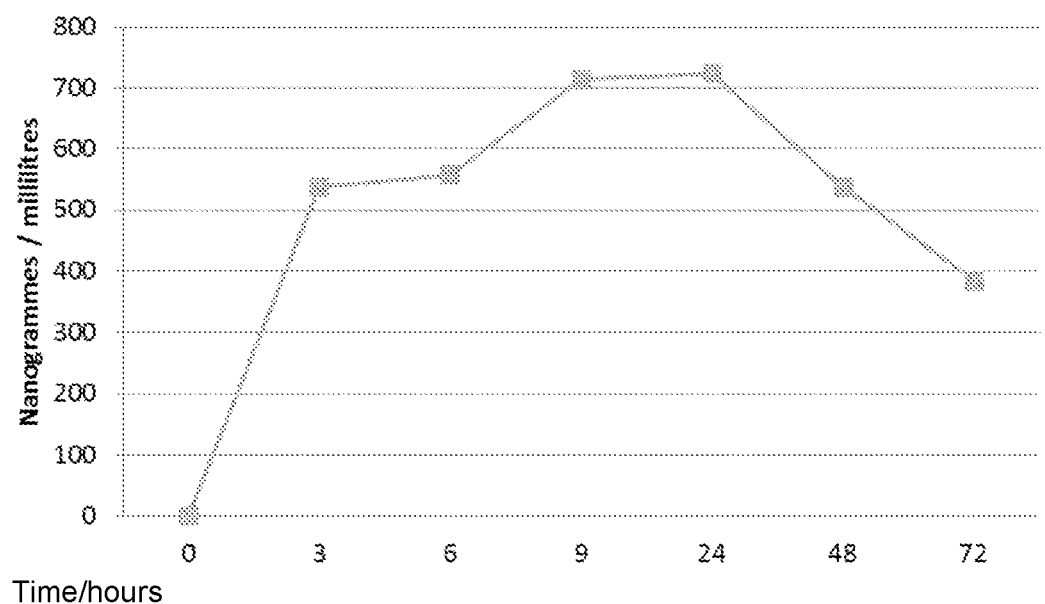
FIG. 2: is a graph representing the comparative bioavailability (or the kinetics) of a curcumin preparation, administered intravenously to a pig.

Indeed, the comparison with a study in the pig after intravenous administration of 0.60 grams of curcumin for 23 kg of live weight, wherein the plasma concentration peaks at 24 hours and remains at a constant level during 10 hours (Table 2, FIG. 2), shows that the curcumin S1 level, thanks to the presence of *spirulina* or *spirulina* extracts, exhibits a very good bioavailability after oral administration with reduced effects of excretion and consequently a more rapid plasma concentration peak (12 hours) that remains for at least 12 hours.

TABLE 2

Curcumin concentration in the plasma after intravenous administration in the pig (for comparison)

| Time (hours) | Nanograms/millilitre |
|---|---|
| 0 | 0 |
| 3 | 537 |
| 6 | 557 |
| 9 | 713 |
| 24 | 724 |
| 48 | 537 |
| 72 | 385 |

Conclusions

The obtained results allow the following conclusions:

1) Curcumin S1 (preparation according to the invention) exhibits a very good bioavailability of the curcumin with a plasmatic half-life of at least 24 hours, after a single oral administration.

2) The pharmacokinetics of the orally administered curcumin S1 are similar to the kinetics of a curcumin used intravenously (in the pig).

The invention claimed is:

1. A method for improving the bioavailability of orally administered curcumin in an animal or human, the method comprising:
   orally administering within 1 hour curcumin in a quantity ranging between 0.1 and 20 mg/kg body weight of the animal or human; and
   orally administering within the 1 hour an effective quantity of
   (i) *spirulina*, or
   (ii) one or more *spirulina* extracts, or
   (iii) *spirulina* and one or more *spirulina* extracts,
   wherein the curcumin exhibits a plasmatic half-life of at least 24 hours, after oral administration of the curcumin.

2. The method according to claim 1, wherein the animal comprises a horse, pig, dog, or cat.

3. The method according to claim 1, wherein the curcumin is administered as at least one of an antioxidant, antiseptic, antibacterial, and anti-inflammatory agent.

4. The method according to claim 1, wherein the curcumin is administered for the treatment or the prevention of cancer, cardiovascular diseases, diabetes, arthritis, neurological diseases, or Crohn's disease.

5. The method according to claim 1, wherein a weight ratio of the (i) *spirulina*, or (ii) one or more *spirulina* extracts, or (iii) *spirulina* and one or more *spirulina* extracts: curcumin is between 20:1 and 1:3.

6. The method according to claim 1, wherein a weight ratio of the (i) *spirulina*, or (ii) one or more *spirulina* extracts, or (iii) *spirulina* and one or more *spirulina* extracts: curcumin is between 10:2 and 1:2.

7. The method according to claim 1, wherein a weight ratio of the (i) *spirulina*, or (ii) one or more *spirulina* extracts, or (iii) *spirulina* and one or more *spirulina* extracts: curcumin is between 8:3 and 3:4.

8. The method according to claim 1, wherein a quantity of *spirulina* ranges between 0.1 and 20 mg/kg body weight of the animal or human.

9. The method according to claim 1, wherein a quantity of *spirulina* ranges between 0.5 and 15 mg/kg body weight of the animal or human.

10. The method according to claim 1, wherein a quantity of *spirulina* ranges between 1 and 10 mg/kg body weight of the animal or human.

11. The method according to claim 1, wherein the curcumin is administered as a food supplement in the field of animal or human nutrition.

12. The method according to claim 1, wherein administration of the curcumin is within half an hour and administration. of the (i) *spirulina*, or (ii) one or more *spirulina* extracts, or (iii) *spirulina* and one or more *spirulina* extracts is within the half an hour.

13. The method according to claim 1, comprising sequentially administering the curcumin and administering the (i) *spirulina*, or (ii) one or more *spirulina* extracts, or (iii) *spirulina* and one or more *spirulina* extracts.

14. The method according to claim 13, comprising administering the (i) *spirulina*, or (ii) one or more *spirulina* extracts, or (iii) *spirulina* and one or more *spirulina* extracts before administering the curcumin.

15. The method according to claim 1, comprising administering the curcumin and administering the (i) *spirulina*, or (ii) one or more *spirulina* extracts, or (iii) *spirulina* and one or more *spirulina* extracts in a single dose.

* * * * *

UNITED STATES PATENT AND TRADEMARK OFFICE
CERTIFICATE OF CORRECTION

| | |
|---|---|
| PATENT NO. | : 12,042,520 B2 |
| APPLICATION NO. | : 15/542371 |
| DATED | : July 23, 2024 |
| INVENTOR(S) | : Antonello Fresu |

It is certified that error appears in the above-identified patent and that said Letters Patent is hereby corrected as shown below:

On the Title Page

For Item (71) the Applicant:
Please delete "SOLUVEG SA, Luxembourg (LU)"
And replace with -- GIANLUCA FRESU, Le Bosc Roger en Roumois (FR) --

Signed and Sealed this
Twentieth Day of August, 2024

Katherine Kelly Vidal
*Director of the United States Patent and Trademark Office*